United States Patent
Bosch et al.

(10) Patent No.: US 6,634,210 B1
(45) Date of Patent: Oct. 21, 2003

(54) PARTICULATE SENSOR SYSTEM

(75) Inventors: Russel H. Bosch, Gaines, MI (US); Da Yu Wang, Troy, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/125,236

(22) Filed: Apr. 17, 2002

(51) Int. Cl.⁷ .......................... G01N 27/04; G01N 37/00
(52) U.S. Cl. .................. 73/23.33; 73/28.01; 73/31.05; 204/426; 204/428
(58) Field of Search .......................... 73/865.5, 866.5, 73/23.31, 23.33, 28.01, 31.05, 31.06; 204/424–428

(56) References Cited

U.S. PATENT DOCUMENTS

| | | | | |
|---|---|---|---|---|
| 3,886,785 A | * | 6/1975 | Stadler et al. | 324/71.5 |
| 4,193,965 A | * | 3/1980 | Cullingford et al. | 422/95 |
| 4,283,261 A | * | 8/1981 | Maurer et al. | 204/408 |
| 4,294,679 A | * | 10/1981 | Maurer et al. | 204/426 |
| 4,295,376 A | * | 10/1981 | Bell | 361/283.3 |
| 4,300,990 A | * | 11/1981 | Maurer | 204/412 |
| 4,307,061 A | | 12/1981 | Sarholz | 422/94 |
| 4,389,373 A | * | 6/1983 | Linder et al. | 324/465 |
| 4,399,424 A | * | 8/1983 | Rigby | 338/308 |
| 4,567,750 A | | 2/1986 | Artmann | 73/28 |
| 4,579,643 A | * | 4/1986 | Mase et al. | 204/424 |
| 4,647,364 A | * | 3/1987 | Mase et al. | 204/412 |
| 4,713,646 A | * | 12/1987 | Sunano et al. | 338/34 |
| 4,839,019 A | | 6/1989 | Takahama et al. | 204/425 |
| 4,947,125 A | * | 8/1990 | De Pous | 324/459 |
| 5,522,979 A | * | 6/1996 | Tatumoto et al. | 204/429 |
| 5,578,271 A | * | 11/1996 | Simon et al. | 422/54 |
| 5,827,415 A | * | 10/1998 | Gur et al. | 204/426 |
| 5,907,278 A | | 5/1999 | Park et al. | 340/450.3 |
| 6,067,843 A | * | 5/2000 | Hafele et al. | 338/273 |
| 6,107,603 A | | 8/2000 | Dementhon et al. | 219/202 |
| 6,136,170 A | * | 10/2000 | Inoue et al. | 204/408 |
| 6,300,576 B1 | | 10/2001 | Nakamura et al. | 174/261 |
| 6,327,891 B1 | * | 12/2001 | Noda et al. | 204/424 |
| 2001/0035044 A1 | * | 11/2001 | Larsson et al. | 73/28.01 |
| 2001/0051108 A1 | | 12/2001 | Schonauer | 422/68.1 |
| 2002/0036138 A1 | * | 3/2002 | Kuroki et al. | 204/426 |

FOREIGN PATENT DOCUMENTS

| | | | | |
|---|---|---|---|---|
| JP | 63103959 A | * | 5/1988 | G01N/27/12 |
| JP | 02263145 A | * | 10/1990 | G01N/27/12 |

* cited by examiner

*Primary Examiner*—Hezron Williams
*Assistant Examiner*—David Rogers
(74) *Attorney, Agent, or Firm*—Vincent A. Cichosz (57) ABSTRACT

One embodiment of a particulate sensor system; comprises a first sensing electrode and a second sensing electrode in thermal and electrical communication with a heater wherein the first sensing electrode and the second sensing electrode are disposed on the same side of an electrode substrate. One embodiment of a method for operating a particulate sensor system comprises introducing a gas stream to a sensor; monitoring the resistance between the first sensing electrode and the second sensing electrode, and increasing the temperature of the sensor when the resistance is greater than or equal to a first selected level. One embodiment of a method for operating a filter system comprises exposing a sensor to a pre-selected number of self-regeneration cycles, and increasing the temperature of the filter system.

10 Claims, 4 Drawing Sheets

PARTICULATE SENSOR SYSTEM

BACKGROUND OF THE INVENTION

The present disclosure relates to a self-regenerating particulate sensor, and more particularly, to a self-regenerating sensor capable of detecting particulates emitted from an exhaust gas. Incomplete combustion of heavy hydrocarbon compounds, such as heavy oils, diesel oil, and the like leads to particulate formation. In the operation of internal combustion engines, "smoking" of the engine leads to ambient air pollution although the carbon monoxide and hydrocarbon emission of the exhaust gases from the internal combustion engine itself are very low. It is, therefore, desirable to detect the formation of particulates in the exhaust of the engine and to provide an output signal that can then be used to indicate the presence of particulates and further to be used as a sensing or control signal, for example in a control loop, to automatically adjust air, or the supply of fuel for complete combustion and to prevent excess particulate formation.

Currently exhaust gases can be sensed by optical sensors; however, such sensors are more suited to fixed locations, for example smokestacks, and are not readily adaptable to automotive use, particularly in view of the rugged and highly variable ambient operating conditions associated with automotive use, including wide swings in temperature, temperature gradients, shock, vibration, and the like. It would, therefore, be desirable to provide a more robust sensor capable of directly sensing exhaust particulates.

In the past, a sensing plate has been used for detecting exhaust particulates, wherein the sensing plate changes the electrical conductivity of a sensor by the formation of a carbon bridge between electrodes. To refresh the sensor, the deposited particulates are burned off by means of a catalyst with extra oxygen in the engine exhaust. Such sensors, however, are not completely practical because the strong reduction effect of the particulates can damage the electrode and detach the electrode from the sensing plane. Current sensors are furthermore unable to control both the temperature surrounding the sensor and the rate of the exhaust flow. This inability is disadvantageous as it allows for the condensation of humidity or moisture on the sensor, which leads to the gradual deterioration of the sensor; thus preventing the sensor from controlling the particulate deposition process, which in turn prevents the sensor from being a direct mechanism by which particulates may be removed from the exhaust. A further problem with current sensors is that they are primarily limited to use with direct current methods of sensing conductivity. Such methods are problematic in that the electrical properties are highly non-liner, thereby making it difficult to control the rate of exhaust flow.

SUMMARY OF THE INVENTION

Disclosed herein is a particulate sensor system, comprising a non-ionically conductive substrate, a non-ionically conductive porous protective layer, a heater, a first sensing electrode and a second sensing electrode; the first and second sensing electrodes being in thermal and electrical communication with the heater; the first and second sensing electrodes being disposed on the same side of the substrate; and the porous protective layer disposed on the electrodes on a surface of the electrodes that is sensing particles.

Further disclosed is a method for operating a particulate sensor system comprising introducing a gas stream to a sensor; monitoring the resistance between the first sensing electrode and the second sensing electrode, and increasing the temperature of the sensor when the resistance is greater than or equal to a first selected level.

Further disclosed is a method for operating a filter system comprising exposing a sensor to a pre-selected number of self-regeneration cycles, and increasing the temperature of the filter system.

The above described and other features are exemplified by the following figures and detailed description.

BRIEF DESCRIPTION OF THE DRAWINGS

Referring now to the figures, which are exemplary embodiments, and wherein the like elements are numbered alike.

DESCRIPTION OF THE PREFERRED EMBODIMENT

The present disclosure relates to a particulate sensor system capable of self-regeneration and for use as a sensing or control signal to automatically remove particulate matter from exhaust emission devices. The particulate sensor system comprises a sensor in electrical communication with a sensor circuit, which operates to detect the level of particulate matter in the environment surrounding the sensor. The particulate sensor system may be calibrated to detect a specific amount of particulate accumulation on the sensor, at which point the particulate sensor system removes the particulates (self-regeneration) by signaling a heater disposed in the sensor. Additionally, the particulate sensor system may be designed such that after a predetermined number of self-regeneration cycles, particles condensed on an exhaust system can also be removed. It is noted that each self-regeneration cycle can be determined based on the size dimensions of the sensor; in general, the smaller the sensing area (e.g., the substrate surface upon which the sensing electrodes are positioned) and the smaller the volume at the tip of the sensor (e.g., that portion of the sensor where the sensing electrodes are positioned), the less time is needed for each self-regeneration cycle. Additionally, a temperature sensor may be advantageously used to maintain the external temperature surrounding the sensor at a point higher than the condensation point of water but lower than the condensation point of the particulates such that the particulates can condense on the sensor without an accompanying condensation of water. Preferably the external temperature maintained by the heater is above the temperature of water condensation, and below the burn-off temperature of the deposited particulates.

The particulate sensor system can self-regenerate by a signal comprising an electrical communication between at least two sensing electrodes and a heater. A signal is transmitted from the sensing electrodes to the heater when the electrical resistance between the sensing electrodes drops to a predetermined threshold amount. Such a drop in resistance is caused by particulate condensation on the sensor. The signal activates the heater to increase its thermal energy output, thereby causing the removal of the particulates from the sensor. As the particulates are removed from the sensor, the resistance gradually increases. The increasing resistance can be employed to signal the heater to decrease its thermal energy output, or the thermal energy output can be maintained until the resistance reaches a selected level, or thermal energy output may be controlled at timed intervals.

In general, the sensor comprises a sensing element and a heating element, wherein the sensing element may comprise, but is not limited to, at least two sensing electrodes, and optionally a guard electrode; and, wherein the heating element may comprise, but is not limited to, a temperature sensor, and a heater. The sensor may include a multi-layered structure comprising the sensing element, the temperature sensor, the heater, and a combination comprising at least one of the foregoing, contained in a single structure formed, e.g., by multi-layer technology.

The sensing electrodes can include metals, such as, gold, platinum, osmium, rhodium, iridium, ruthenium, aluminum, titanium, zirconium, and the like, as well as, oxides, cermets, alloys, and combinations comprising at least one of the foregoing metals. In an exemplary embodiment, the sensing electrode can comprise a platinum/alumina cermet wherein the platinum is about 90 wt % (weight percent) to about 98 wt % of the sensing electrode, with about 93 wt % to about 95 wt % platinum particularly preferred, where weight percent is based on the total dry weight of the cermet. Each sensing electrode may be composed of the same or different material as the other sensing electrode(s).

The sensing electrodes can be formulated in any fashion. Preferably, however, the sensing electrodes are formed by first preparing an ink paste by mixing an electrode forming-metal powder (e.g., platinum, gold, osmium, rhodium, iridium, ruthenium, aluminum, titanium, zirconium, and the like, or combinations of at least one of the foregoing) with oxides in a sufficient amount of solvent to attain a viscosity suitable for printing. The oxides used to form the sensing electrodes may include those oxides that do not promote the oxidation of particulates and that do not lower the burn-off temperature of the particulates. Non-suitable oxides are, e.g., copper oxide, cerium oxide, and iron oxide. The ink paste forming the sensing electrode can then be applied to an electrode substrate via sputtering, chemical vapor deposition, screen printing, flame spraying, lamination, stenciling, or the like, with screen printing particularly preferred.

The sensing electrodes are preferably disposed onto the electrode substrate such that a constant distance of separation between each sensing electrode is created. The width of the distance separating the sensing electrodes can vary widely, depending upon desired design parameters. A preferred distance comprises a width of separation of about 0.1 to about 0.5 millimeter (mm), with about 0.1 to about 0.3 mm particularly preferred, and about 0.1 mm especially preferred. The distance between the sensing electrodes will allow for a suitable amount of particulate to form between the sensing electrodes, and will also allow for the positioning of a guard electrode between the sensing electrodes where appropriate.

The size and geometry of the sensing electrode is preferably selected to allow for current output sufficient to enable reasonable signal resolution over a wide range of particulate concentrations. Generally, a thickness of about 5 to about 25 micrometers can be employed, with a thickness of about 8 to about 20 micrometers preferred, and about 10 to about 18 micrometers particularly preferred. The sensing electrode can be of any shape, for example, rounded, squared, polygonal, such as square, needle-shaped, round, oblong, interdigital, or the like.

The optional guard electrode is most preferably included in the sensor when an alternating current (AC) method is used to detect conductivity (complex impedance). The AC method is ideally employed where a sensor more sensitive than that obtained using a DC method is desired. The differing sensitivity created by AC or DC methods is a result of the way in which the particulates are detected. For example, sensing, and hence, quantification, of particulate accumulation by the DC method, requires that the particulates be in direct physical contact (bridging) with other deposited particulates. Therefore, particulate sensing is limited to those deposited particulates in direct contact with other deposited particulates. Such direct contact occurs only when a sufficient amount of particulates deposit on the surface between the two electrodes. When particulate deposition is insufficient, and there is not enough direct particle contacts to form a direct conducting bridge between the electrodes, there is no DC current flow, and the sensor cannot detect the presence of deposited particulates. The AC method, however, can detect a greater range of particulates as AC can conduct current among the non-contacting particulates through capacitance effect, and hence, can sense non-bridged particulates. In this way, a full range (e.g., up to about 100%) of particulate concentrations can be measured using an AC method as compared to a range of about 15–25% detected when using a DC method (numbers are based on the commonly known percolation theory). In general, the higher the AC frequency, the more sensitive the sensor.

The AC guard electrode is preferably disposed along the length of the electrode substrate, and is preferably positioned between the sensing electrodes up to the area wherein the deposited particulates can be detected. The guard electrode can eliminate any stray capacitance between the sensing electrodes from the background measurement data and thereby improve the signal to noise ratio. The use of AC detection can also protect the two measurement electrodes from direct exposure to the exhaust gas. Under the AC method, the sensing electrodes can be covered with an over-layer, preferably a thin over-layer, (e.g., a thickness of up to about 60 micrometers), of a dense glass (glazing materials), oxides (e.g., alumina), or combinations comprising at least one of the foregoing. The over-layer can protect the sensing electrodes against reduction of the particulates when they are burned off. Typically, when the particulates are burned off, oxygen is consumed, thereby creating a reducing atmosphere locally. This reducing atmosphere, in turn, can reduce the weak oxide bonding between the sensing electrodes and the substrate, and can de-bond the sensing electrodes from the substrate. An over-layer, however, can protect the sensing electrodes, and the AC frequency current can still flow through the over-layer to engage the deposited particulates. The over-layer can be done with doctor-bladed cast tape, or with commercial glazing products. Preferably, the over-layer comprises a dense glass or oxide to hinder the reducing atmosphere from penetrating underneath the sensing electrodes where the sensing electrodes contact the substrate.

Both the heater and the temperature sensor, forming in whole or in part, the heating element, can comprise various materials. Possible materials include platinum, gold, palladium, and the like; and alloys, oxides, and combinations comprising at least one of the foregoing materials, with platinum/alumina, platinum/palladium, platinum, and palladium preferred. The heater and temperature sensor can be applied to the sensor in any fashion, such as by sputtering, chemical vapor deposition, screen printing, flame spraying, lamination, and stenciling among others where screen printing is particularly preferred. Furthermore, the heater can comprise a thickness of about 3 to about 50 micrometers, with about 5 to about 30 micrometers preferred, and about 10 to about 20 micrometers more preferred.

The sensor may further comprise various substrates useful in electrically isolating and protecting the sensing element and the heating element from the temperature surrounding the sensor and/or from the thermal reduction of the condensed particulates during the self-regeneration cycles. The substrates include, but are not limited to, an electrode protective layer, an electrode substrate, an isolation layer, an insulating temperature substrate, a heater substrate, insulating substrates, wherein the number of insulating substrates is sufficient to prevent disruptive ionic or electrical communication between the heating element and the sensing electrode (e.g., preferably about 2 to about 3 insulating substrates), and combinations comprising at least one of the foregoing.

The substrates can comprise non-ionically conducting, electrically insulating materials. Possible electrically insulating materials include oxides, such as alumina, zirconia, yttria, lanthanum oxide, silica, and combinations comprising at least one of the foregoing, or any like material capable of inhibiting electrical communication and providing physical protection, wherein alumina is particularly preferred. In order to hinder electrical communication between the components of the sensor, the substrates are preferably composed of a high purity oxide; e.g., less than about 10.0 wt % impurities, with less than about 8.0 wt % preferred, and less than about 5.0 wt % more preferred, wherein the weight percent of the impurities is based on the total weight of the substrate. Although the composition of the individual substrates can vary, preferably they comprise a material having substantially similar coefficients of thermal expansion, shrinkage characteristics, and chemical compatibility in order to minimize, if not eliminate, delamination and other processing problems. Alkaline (e.g., sodium, potassium, lithium, and the like) oxides should be avoided as they can be easily reduced to form impurities in the heater, temperature sensor, and the sensing electrodes.

In general, each of the substrates can be of sufficient size to support the entire length of the sensing electrodes, the temperature sensor, and/or the heater. The thickness of each substrate can be determined based on the desired thermal response time of the self-regeneration cycle, where shorter thermal response times require a smaller thickness. Preferably, the thickness of each substrate can be up to about 200 micrometers thick, with a thickness of about 50 to about 180 micrometers more preferred, and about 140 to about 160 micrometers especially preferred. The substrates can be formed using ceramic tape casting methods, and the like.

Any number of the substrates can be porous, dense, or both porous and dense. The porosity or the diameter of the pores can be controlled to limit the various sizes of particulates that can reach the sensing electrodes, and to limit the size of particulates that can penetrate and trap within the porous layer. In general, larger-sized particulates (e.g., particles having a diameter along the major axis equal to or greater than about 5 micrometers) interfere with current conduction more than do smaller-sized particulates (e.g., particles having a diameter along the major axis less than about 5 micrometers). Therefore, where more precise conductance measurements are desired, it is especially desirable to exclude the larger particulates from accumulating onto or between the sensing electrodes. Such exclusion can be achieved by controlling the size and/or the number of pores on the substrate, and/or by controlling the internal tortuousness of the substrate. Here, tortuousness is defined as the effective path length through the connected pores per standard thickness of the layer.

Pore size can be controlled by the size of the fugitive materials used, e.g., by controlling the size of carbon black or graphite, where fugitive materials are those materials that burn off at high temperatures leaving behind pores with controlled sizes. Tortuousness depends on the texture of the substrate-forming oxide powder used to form the substrate. Texture, in turn, can be controlled by firing the substrate-forming oxide powder at a high temperature to coarsen the substrate-forming powder, and then sieving the substrate-forming metal powder to the right size range for slurry making.

Preferably, where the substrate comprises the electrode protective layer, there is a space gap (e.g., about 10 to about 50 micrometers) between the electrode protective layer and the sensing electrodes to allow for the free deposition of particulates after penetrating the porous electrode protective layer. Applying a fugitive layer between the sensing electrode area and the porous layer, which can be burned off during the firing stage, can create the space gap. Screen printing can be used to deposit such layers.

The sensor may further comprise various leads responsible for electrically communicating the sensor with the sensor circuit. One end of each sensing electrode, one end of the temperature sensor, and one end of the heater preferably has a connecting point to which one end of at least one lead may be attached. Preferably, each sensing electrode is electrically connected with at least one lead extending from one end of each sensing electrode to via holes formed on the isolation layer; the temperature sensor is electrically connected with at least one lead extending from one end of temperature sensor to via holes formed on the insulating temperature substrate; and the heater is electrically connected with at least one lead extending from one end of the heater to via holes formed on the heater substrate. The via holes formed on the above substrates serve to provide a mechanism for electrically connecting the leads to a top contact pad and a bottom contact pad positioned on the exterior of the sensor. The contact pads provide a contact point between the sensor and the sensor circuit. In a preferred embodiment, the via holes are formed at the end portion of the sensor where the opposite end of the sensor is the tip.

The via holes, top contact pad, and bottom contact pad comprise electrically conductive materials. A general method for forming the via-holed substrate is described in U.S. Pat. No. 6,300,576. For example, each via hole is formed by penetrating the substrate to form a through-hole as the via hole at the position for wiring, filling the through-hole with a conducting paste, and curing the conducting paste while the substrate is shaped and cured under heat in a heating/pressing step. The conducting paste can be prepared as a paste using conducting particles, a thermosetting resin solution, and, if necessary, a solvent. The thermosetting resin can be selected from resins that can be cured simultaneously in the step of heating/pressing the substrate. An epoxy resin, thermosetting polybutadiene resin, phenol resin, or polyimide resin is preferably used.

For the conducting particles, a conducting particle-forming powder of a metal material that is stable and has a low specific resistance and low mutual contact resistance is preferably used. For example, a powder of gold, silver, copper, platinum, palladium, lead, tin, nickel, and combinations comprising at least one of the foregoing is preferably used.

After acquiring the components of the sensor, the sensor is preferably constructed according to thick film multilayer technology such that the thickness of the sensor allows for good thermal response time toward the thermal cycle of sensor regeneration. A preferable thickness is about 0.1 to about 3.0 millimeter (mm), with about 0.15 to about 2.5 mm particularly preferred, and about 0.3 to about 1.22 mm especially preferred. To increase the thermal mechanical strength (thermal shock) of the sensor, the tip of the sensor is preferably as small as possible, yet large enough for ease of manufacturing. Therefore, the tip of the device can comprise a length of about 0.5 to about 4.5 mm, with about 1.0 to about 4.0 mm preferred, and about 1.0 to about 2.0 mm more preferred. To accommodate the top and bottom contact pads at the end portion of the device where thermal shock is of no concern, the width of the sensor can be about 4 to about 8.5 mm, with about 4.5 to about 8.0 mm preferred, and about 5.0 to about 6.0 mm more preferred.

Figure 1:
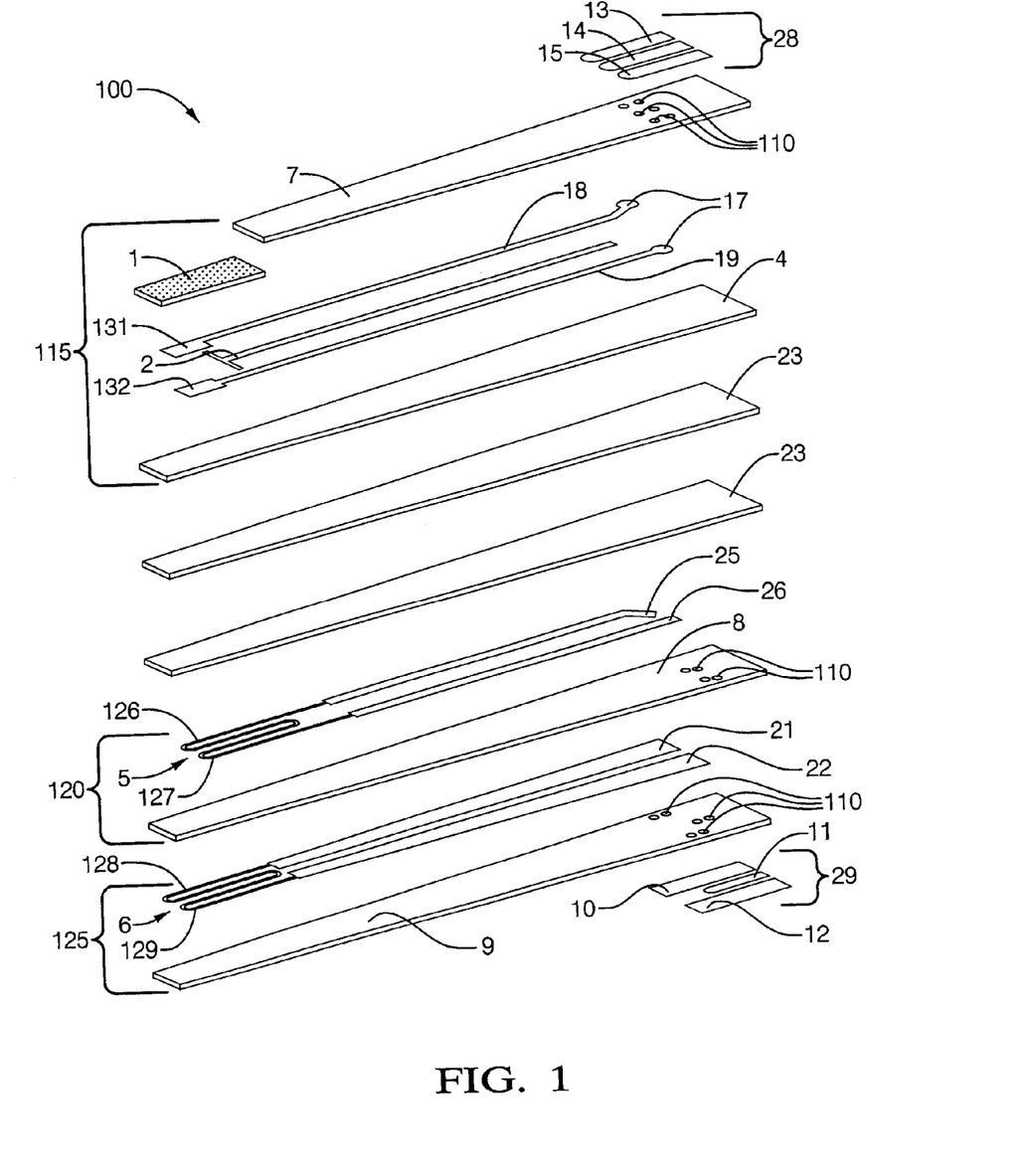
FIG. 1 is a schematic showing an exemplary embodiment of the sensor.

Referring to the drawings, FIG. 1 shows an exploded view of a typical sensor 100. The sensor is a multi-layered device having a plurality of electrically insulating layers or substrates, e.g., 4, 7, 23, 8, and 9 interspersed between the operative electrically conductive elements of the sensor. The sensor includes an electrode substrate 4 with a first sensing electrode 131 and a second sensing electrode 132 wherein each is capable of being mounted on or fixed to the same side of the electrode substrate 4. An optional guard electrode 2 may be included. This guard electrode is capable of being mounted or fixed between the sensing electrodes and electrically connected to a ground (not shown). An electrode protective layer 1 is mounted or fixed over the sensing electrodes 131 and 132 and the guard electrode 2. This entire construction forms an electrode sensor element 115. A temperature sensor 5 is mounted on an insulating temperature substrate 8 to form a temperature sensor element 120, and a heater 6 is mounted on a heater substrate 9 to form a heater element 125. A plurality of insulating substrates 23 is mounted between the temperature sensor element 120 and the electrode sensor element 115 to electrically isolate the first sensing electrode 131 and the second sensing electrode 132 from the temperature sensor 5 and the heater 6. The first sensing electrode 131 is electrically communicated with one end of a first measuring lead 18, which extends from the first sensing electrode 131 and is electrically communicated to via holes 110 formed on the isolation layer 7. The second sensing electrode 132 is electrically communicated with one end of a second measuring lead 19, which extends from the second sensing electrode 132 and is electrically communicated to via holes 110 formed on the isolation layer 7. Guard electrode 2 is disposed across the electrode substrate 4 wherein one end of the guard electrode 2 is electrically communicated with via holes 110 formed on the isolation layer 7.

Electrode protective layer 1 and electrode substrate 4 are non-movably associated with the first sensing electrode 131, the second sensing electrode 132, and guard electrode 2 to secure the first sensing electrode 131, the second sensing electrode 132, and the guard electrode 2 to the sensor 100. A dense reduction protection over-layer on top of electrodes 131 and 132 (not shown in FIG. 1) can be introduced when an AC measurement method is used. Such security is preferred as particulates condense on the sensor to create a strong reduction effect of the particulate matter, which can otherwise damage the sensing electrodes. Electrode substrate 4 is also non-movably associated with guard electrode 2 so as to secure guard electrode 2 in the sensor 100.

In accordance with a first embodiment, temperature sensor 5 comprises a first temperature sensor end 126 and a second temperature sensor end 127. One end of a first temperature sensing lead 25 is electrically communicated with the first temperature sensor end 126 and extends to and is connected with via holes 110 formed on the insulating temperature substrate 8. One end of a second temperature sensing lead 26 is electrically communicated with the second temperature sensor end 127 and extends to and is communicated with via holes 110 formed on the insulating temperature substrate 8. Preferably, the insulating temperature substrate 8 is non-movably associated with the temperature sensor 5 and the heater 6 so as to electrically isolate the temperature sensor 5 from the heater 6.

Also in accordance with a first embodiment, heater 6 includes a first heater end 128 and a second heater end 129. One end of a first heater element lead 21 is electrically communicated with the first heater end 128 and extends to and is connected with via holes 110 formed on the insulating temperature substrate 8 and the heater substrate 9. One end of a second heater element lead 22 is electrically communicated with the second heater end 129 and extends to and is communicated with via holes 110 formed on the insulating temperature substrate 8 and the heater substrate 9. In addition, sensor 100 preferably includes a heater substrate 9 nonmovably associated with heater 6 so as to electrically isolate heater 6 from a second contact pad 29.

In accordance with a first embodiment, the first measuring lead 18, second measuring lead 19, and the guard electrode 2 are electrically communicated with a first contact pad 28, wherein the first contact pad 28 comprises a first ground terminal 13, a first resistance measurement terminal 14, and a second power terminal 15. In an exemplary embodiment, the first measuring lead 18 is preferably electrically communicated with the first ground terminal 13, the second measuring lead 19 is preferably electrically communicated with the second power terminal 15, and the guard electrode 2 is electrically communicated with the first resistance measurement terminal 14.

Also in accordance with an exemplary embodiment, the first heater element lead 21 is preferably electrically communicated with the first temperature sensing lead 25 such that the temperature sensor can serve as an alkaline impurity getter. By removing the alkaline impurities condensed on the heater, the temperature sensor serves to prolong the usability of both the heater and the sensing electrodes. While not damaging the temperature sensor since the accumulated alkaline impurity does not change the temperature sensor's total resistive characteristics to any significant degree. The electrical communication between heater 6 and temperature sensor 5 comprises connecting a first temperature sensing lead 25 with the first heater element lead 21, such that the lead from the temperature sensor is electrically connected to the negative polarity lead of the heater. The electrical connection may be made by way of via holes 110 formed on the insulating temperature substrate 8.

Furthermore, in a first embodiment, the second temperature sensing lead 26 and second heater element lead 22 are electrically connected to a second contact pad 29. The second contact pad 29 comprises a second ground terminal 10, a second resistance measurement terminal 11, and a first power terminal 12.

In an exemplary embodiment, the second heater element lead 22 can be electrically communicated with the first power terminal 12; the second temperature sensing lead 26 can be electrically communicated with the second resistance measurement terminal 11; and the first temperature sensing lead 25 can be electrically communicated with the first heater element lead 21, wherein the first heater element lead 21 can also be electrically communicated with the second ground terminal 10.

Figure 2:
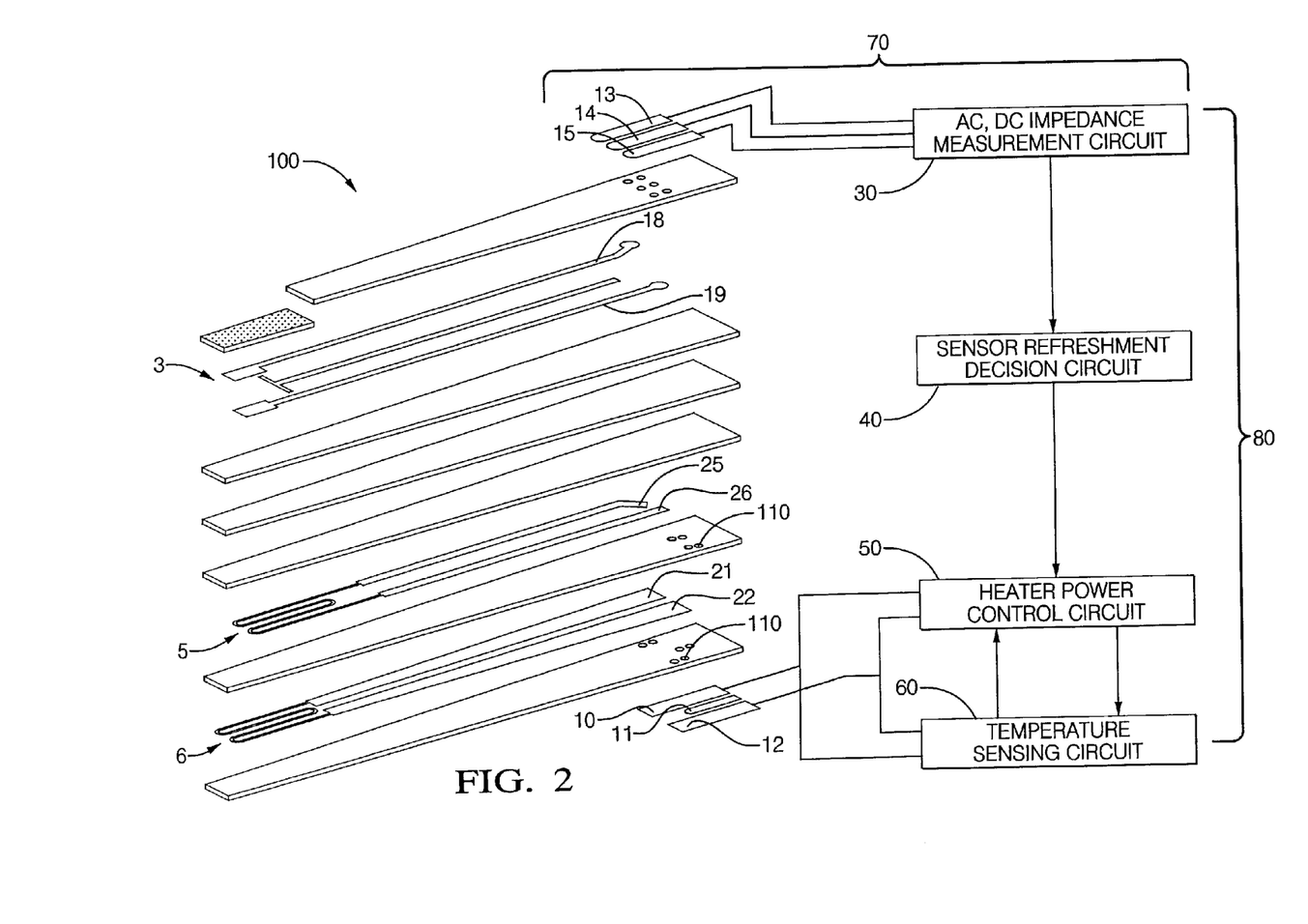
FIG. 2 is a flow diagram showing the circuitry of the particulate sensor system.

A second embodiment of the particulate sensor system 70 is shown in FIG. 2, which depicts the sensor 100 in relation to a sensor circuit 80. As schematically shown in FIG. 2, the first ground terminal 13, the first resistance measurement terminal 14, and the second power terminal 15 are electrically communicated to form the AC/DC (alternating current/direct current) impedance measurement circuit 30. The AC/DC impedance measurement circuit 30 can be a series circuit comprising a resistor, the sensing electrodes, the guard electrode, and a measuring device.

Figure 3:
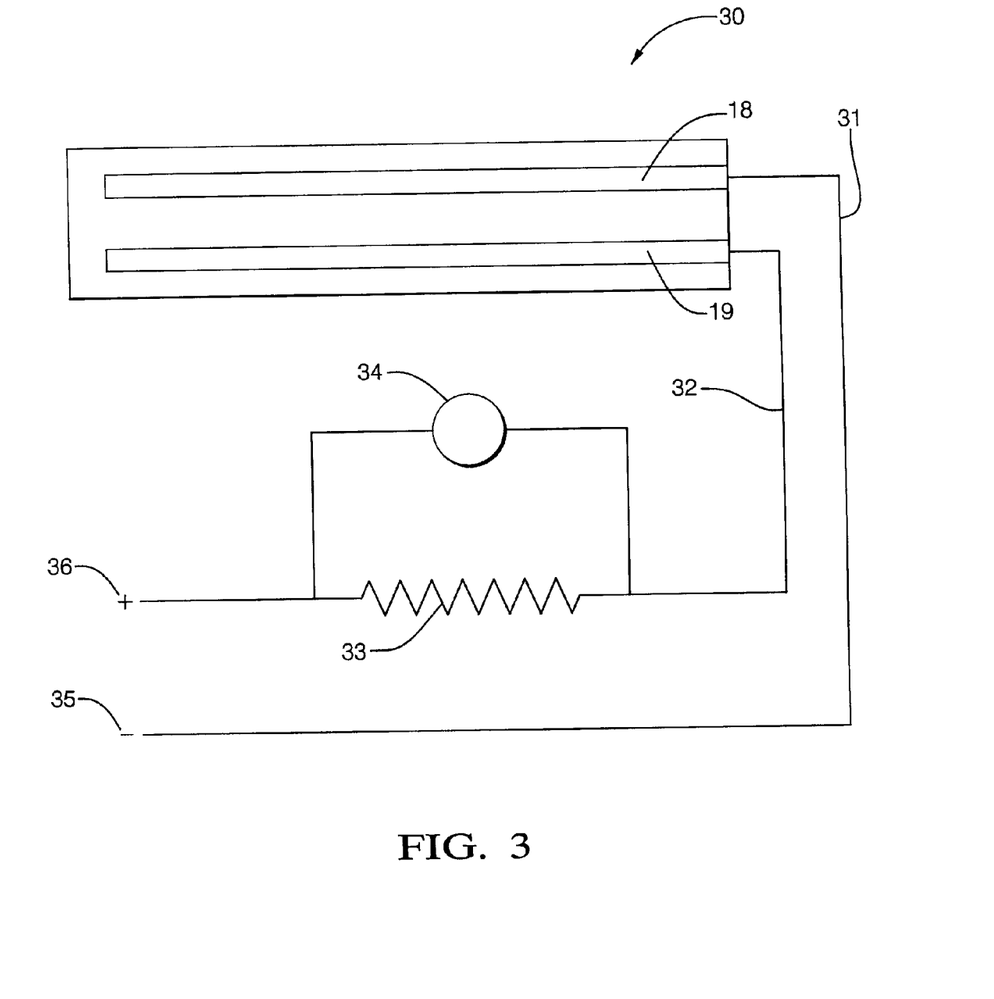
FIG. 3 is a circuit diagram showing the sensing electrodes in series with the resistor.

FIG. 3 depicts an exemplary embodiment of the AC/DC impedance measurement circuit 30. As shown in FIG. 3, the first measuring lead 18 is electrically communicated to a first lead 31. Such a communication may be made by way of via holes formed in the isolation layer wherein a first ground terminal may mediate the electrical communication. The first lead 31 extends from the electrical communication with the first measuring lead 18 to a ground potential 35. Additionally, a second lead 32 is electrically communicated to the second measuring lead 19. Such a communication may be made by way of via holes formed in the isolation layer wherein a first resistance measurement terminal may mediate the electrical communication. The second lead 32 extends from the electrical communication with the second measuring lead 19 to a resistor 33. The resistor 33, in turn, is electrically communicated to a positive/negative terminal 36, and to a measuring device 34. The measuring device 34 can be any device capable of reading the resistance, such as a voltmeter, or an ohmmeter.

In another embodiment of the AC/DC impedance measurement circuit, the guard electrode can be electrically communicated to the resistor by way of the first resistance measurement terminal. Such a connection can be affected by via holes formed in the isolation layer.

FIG. 2 further depicts a sensor refreshment decision circuit 40 in electrical connection with the AC/DC impedance measurement circuit 30 and a heater power control circuit 50. In a preferred embodiment, once the resistance between the first measuring lead 18 and the second measuring lead 19 of the sensing electrodes 3 decreases to a threshold resistance level with design parameters, as determined by the measuring device (not shown) in the AC/DC impedance measurement circuit 30, the sensor refreshment decision circuit 50 emits a signal to the heater power control circuit 50 which, in turn, transmits a signal to the heater 6 to increase its thermal energy output. Such a transmittal by the heater power control circuit 50 to the heater 6 is preferably a result of the electrical communication between the first power terminal 12 and the second heater element lead 22 as affected by via holes 110 formed in the heater substrate 9: The thermal output by the heater 6 is increased to a level sufficient to burn off particulates deposited on and/or between the sensing electrodes 3. Suitable burn-off temperatures may include heating the sensor up about 500° C. to up to about 1,100° C., with up to about 500° C. to up to about 1,000° C. preferred, and up to about 500° C. to up to about 950° C. more preferred. As the particulates are burned off, the resistance between the sensing electrodes 3 rises proportionately until a second predetermined resistance is reached, at which point, the heater power control circuit 50 signals to the heater 9 to reduce its thermal energy output.

In an exemplary embodiment, the particulate sensor system may be calibrated such that after a predetermined number of self-regeneration cycles, (e.g., after the sensing electrodes have signaled the heater to burn off particulates condensed on the sensor), an additional electrical signal may be sent from the particulate sensor system to an additional heater located in an environment rich in exhaust soot condensation, such that the additional heater may burn off the exhaust particulate condensation or may signal the engine to adjust fuel ratios (exhaust temperature) to assist in burning off the condensation. The temperature at which the exhaust soot can typically be burned off is about 500° C. to about 1,100° C.

In an exemplary embodiment the particulate sensor system further comprises a temperature sensing circuit that can continuously control the temperature surrounding the particulate sensor 100. As shown in FIG. 2, the second temperature sensing lead 26 of the temperature sensor 5 is electrically communicated with the second ground terminal 10; the second ground terminal 10 is electrically communicated with the heater power control circuit 50 by way of the temperature sensing circuit 60. The heater power control circuit 50 sends a signal back through the temperature sensing circuit 60 to the heater 6 by way of the electrical communication between the first power terminal 12 and the second heater element lead 22. Preferably the heater 6 is activated by the heater power control circuit 50 when the temperature falls below or at the condensation temperature of water, and is deactivated at a point just lower than the condensation point of the particulates. Suitable deactivation points include, but are not limited to, temperatures of about 125° C. to about 475° C., with about 150° C. to about 450° C. preferred, and about 175° C. to about 425° C. more preferred.

The particulate sensor system is preferably powered by a battery or other power generating device. The power supplied by the battery to the particulate sensor system depends on the current method employed (e.g., AC or DC) and on the degree of sensitivity required. In general, the higher the voltage, or the higher the frequency, the lower the particulate concentration the particulate sensor system can detect. Consequently, for a DC method, the voltage (V) used is preferably about 0.1 V to about 700 V, where 0.1 to about 500 V is more preferred. For an AC method, the frequency used is preferably about 50 kilohertz (kHz) to about 400 kHz, where 100 kHz to about 300 kHz is more preferred.

An exemplary application of the disclosed particulate sensor system is as a signaling device to regenerate filter systems commonly employed to control the amount of pollutants released from the exhaust of diesels and other internal combustion engines. An especially preferred filter system is a particulate sensor system. The particulate sensor system can be calibrated such that upon reaching a specified number of self-regeneration cycles, a control device sends a signal to the particulate sensor system to regenerate itself. Upon receiving the appropriate signal, a heater disposed within the particulate trap can be activated to burn off the particulate deposited on the particulate trap, or more air can be added to the exhaust to burn off the particulates, or to increase the exhaust temperature to ignite the regeneration of the particulate trap.

Figure 4:
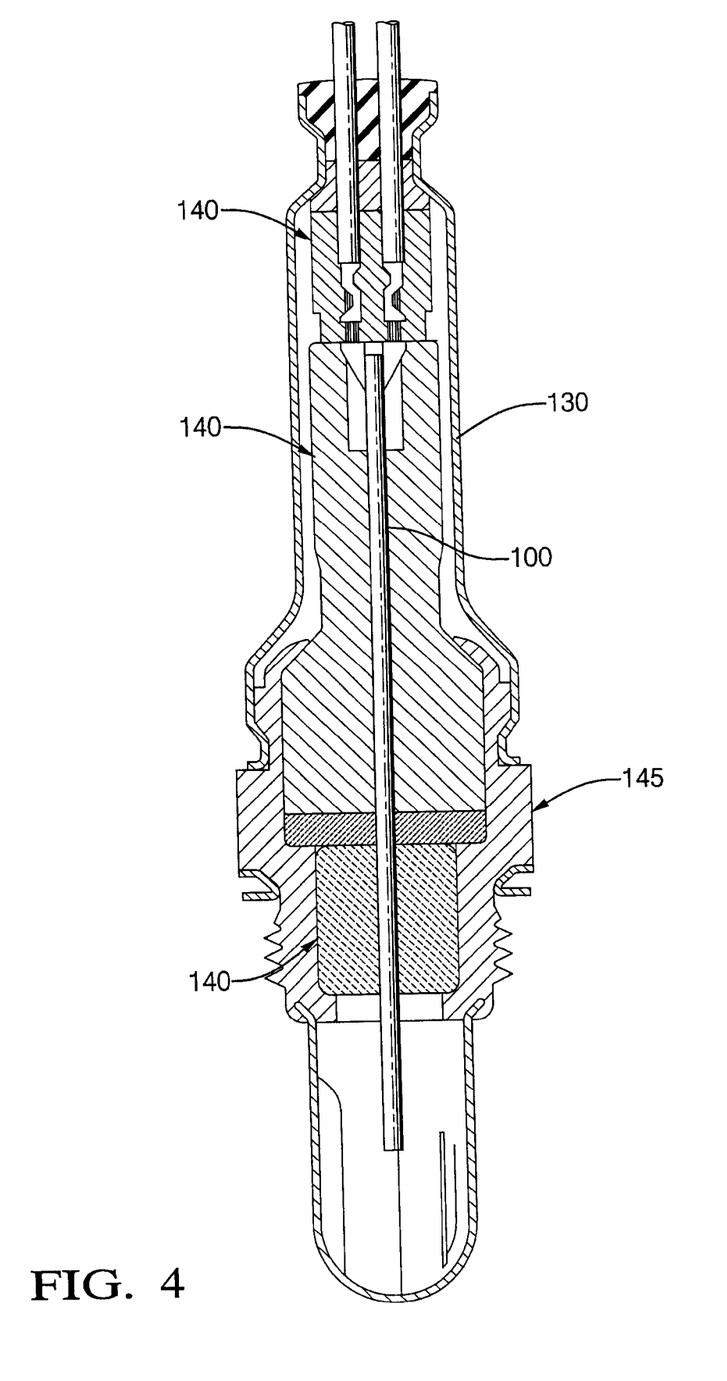
FIG. 4 is a cutaway view an exemplary embodiment of a particulate sensor.

FIG. 4 depicts another embodiment of the particulate sensor. FIG. 4 shows the sensor 100 installed in suitable sockets of metal. As shown in FIG. 4, the sensor can additionally comprise a louvered shield 130. The louvered shield 130 protects an exposed portion of the sensor 100 and has perforations so as to allow flow of the exhaust gases around the sensor. By appropriate design of the louver shield, the amount and velocity of the gas can be regulated to increase the temperature of the sensor. The louvered shield can be exposed to the harsh exhaust gases and therefore is preferably formed from a suitable material such as a stainless steel. Additionally, the louvered shield can be used to control the penetration of small-size particulates. Particulates with sizes greater than about 1 micrometers are more easily sensed by the resistive measurement device. Controlling the louvered shield offers the possibility of sensing the concentration of those particulates smaller than the controlled cut-off size.

As further shown in FIG. 4, introduction of the sensor 100 into the gas stream, the particulate content of which is to be determined, is preferably done by securing the sensor elements themselves in suitable sockets made of metal. The sockets can comprise embedding the sensor 100 in ceramic insulators 140 which in turn are covered by a shell 145. The socket can, directly, form one terminal connection, for example the chassis or ground connection to the ground potential of the power supply source. The other terminal is brought out to a connecting cap. Sockets used in general connection with spark plugs, and shaped similarly thereto, and having spark plug-type threads, are suitable; other socket constructions, for example as used in connection with oxygen-exhaust gas sensors, are also suitable.

The particulate sensor system disclosed herein has several improvements over a sensor that does not comprise a sensor in electrical communication with an external circuit as disclosed herein. The particulate sensor system provides a regenerative on-site mechanism for monitoring and controlling the level of particulate matter contained in the emission of gases, particularly those gases generated in automobiles. The time for the particulate matter condensation onto the sensor and the cleaning of the sensor is monitored and is related to the level of particulate from the engine. The signal for cleaning the sensor can be used to control the engine smoke, engine diagnostics, and particulate trap regeneration. Also, the system of the present disclosure has a relatively small thermal mass that improves the thermal response time of the regeneration of the sensor. The use of an AC resistance measurement method allows for the detection of lower soot concentrations as compared to a DC method. The possible use of a fully dense protection layer on top of the sensing electrodes for the AC method fully protects the electrodes from the reduction power of the soot regeneration, and still allows for the electrodes to sense condensed particulates by the complex impedance measurement.

The pore size controlled porous layers allows the soot measurement to be biased toward smaller sizes of particulate. The controlled shield louvers can decrease the ratio of the gas speeds inside and outside of the louver. In so doing, the larger particulates can be excluded from entering the sensor shield.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A particulate sensor system comprising: a particulate sensor element comprising a non-ionically conductive substrate, a non-ionically conductive porous protective layer, a heater, a first sensing electrode, and a second sensing electrode; said first and second sensing electrodes being in thermal and electrical communication with said heater; said first and second sensing electrodes being disposed on the same side of said substrate; and said porous protective layer disposed on said electrodes in a region of said electrodes that is sensing particles.

2. The particulate sensor system of claim 1, wherein said particulate sensor system further comprises a temperature sensor disposed between said electrode substrate and said heater, and in electrical communication with said heater.

3. The particulate sensor system of claim 1, wherein said particulate sensor system further comprises a louvered shield disposed around said particulate sensor system.

4. The particulate sensor system of claim 1, wherein said first sensing electrode and said second sensing electrode are disposed on said electrode substrate to create a width of separation between said first sensing electrode and said second sensing electrode wherein said width of separation is about 0.1 to about 0.5 millimeters.

5. The particulate sensor system of claim 1, wherein said particulate sensor system further comprises an isolation layer in physical contact with said electrode protective layer.

6. The particulate sensor system of claim 1, further comprising an insulating substrate disposed between said heater and said electrode substrate, on a side of said electrode substrate opposite said first sensing electrode.

7. A particulate sensor system, comprising: a particulate sensor element, the particulate sensor element comprising:
a first sensing electrode and a second sensing electrode in thermal and electrical communication with a heater wherein said first sensing electrode and said second sensing electrode are disposed on a same side of a non-ionically conducting electrode substrate;
a porous electrode protective layer disposed on said first sensing electrode and said second sensing electrode;
an isolation layer in physical contact with said electrode protective layer; and
a guard electrode disposed on said electrode substrate and positioned between and electrically isolated from said first sensing electrode and said second sensing electrode.

8. The particulate sensor system of claim 7, wherein an over-layer is disposed on said first sensing electrode and said second sensing electrode.

9. The particulate sensor system of claim 8, wherein said over-layer comprises a material selected from the group consisting of dense glass, oxides, and combinations comprising at least one of the foregoing materials.

10. The particulate sensor system of claim 9, wherein said over-layer has a thickness of up to about 60 micrometers.

* * * * *